United States Patent [19]

Fridman et al.

[11] Patent Number: 5,264,592
[45] Date of Patent: Nov. 23, 1993

[54] LACTIDE MELT RECRYSTALLIZATION

[75] Inventors: Israel D. Fridman, Belmont; John Kwok, Holden, both of Mass.

[73] Assignee: Camelot Technologies Inc., Leominster, Mass.

[21] Appl. No.: 941,678

[22] Filed: Sep. 8, 1992

[51] Int. Cl.⁵ ............................................. C07D 319/12
[52] U.S. Cl. ..................................................... 549/274
[58] Field of Search ........................................ 549/274

[56] References Cited

U.S. PATENT DOCUMENTS 5,127,921  7/1992  Griffiths ........................... 23/295 R

FOREIGN PATENT DOCUMENTS 0261572  9/1987  European Pat. Off. .
0275581  7/1988  European Pat. Off. .
PCT/WO90/-
01521  2/1990  PCT Int'l Appl. .

Primary Examiner—C. Warren Ivy
Assistant Examiner—A. A. Owens
Attorney, Agent, or Firm—Bruce E. Harang

[57] ABSTRACT

Generally, polylactic acid is prepared by the ring opening polymerization of lactide. However, to obtain a high molecular weight polylactic acid it is necessary to start with a lactide having a high degree of purity. Lactide may be economically brought to the required degree of purity using melt recrystallization techniques.

17 Claims, 6 Drawing Sheets

L, M LACTIDE, LACTIC ACID PHASE DIAGRAM
Van't Hoff Equation

LACTIDE MELT RECRYSTALLIZATION

FIELD OF THE INVENTION

The present invention relates to the purification of lactide for the polymerization of polylactic acid. More particularly the present provides an economical process for the preparation of lactide having the required degree of purity for polymerization to high molecular weight polylactic acid.

BACKGROUND OF THE INVENTION

WO 90/01521 in the name of Battelle Memorial Institute published Feb. 22, 1990 discusses the polymerization of polylactic acid while maintaining residual monomer in the polymer to act as a plasticizer. The disclosure is of interest in that there is a fairly lengthy discussion of the prior art processes used to prepare polylactic acid. Most of the processes described as prior art disclose polymerizing lactic acid or lactide. There is no strong discussion regarding the preparation of lactide.

European Patent Application 0 261 572 in the name of Boehringer Ingelheim KG published Sep. 16, 1987 discloses a process in which polylactic acid is heated in the presence of a catalyst, and under vacuum, at temperatures from 130° to 230° C. and lactide is distilled off. The polylactic acid should have a molecular weight from 400 to 2,000, preferably from 500-800. In the polymerization of lactic acid, lactic acid is first heated. Initially low molecular weight polylactic acid forms. However, as the reaction proceeds the low molecular weight polylactic acid begins to depolymerize and form lactide. Then an equilibrium is established between lactide, lactic acid, water and low molecular weight polylactic acid. The result is that it is very difficult to directly polymerize high molecular weight polylactic acid from lactic acid. Rather, one must first prepare lactide and then subject it to a ring opening polymerization. However, the above noted equilibrium makes it difficult to produce a relatively pure stream of lactide from an equilibrium mixture.

Lactide may be in the form of several different isomers. It may be an l-, or m-isomer. In preparing polylactic acid it is generally desirable to have a polymer containing a high amount of l-isomer. The physical properties of the l-isomer and particularly the heat distortion temperature under load are better for this type of polymer.

U.S. patent application Ser. No. 659,567 filed Feb. 22, 1991, (corresponding to Canadian Patent Application No. 2,056,549 filed Nov. 28, 1991), now U.S. Pat. No. 5,136,017, discloses a continuous process for the polymerization of lactide to polylactic acid. The patent does not disclose any process for the purification of lactide to the degree necessary to polymerize lactide to produce high molecular weight polylactic acid.

Generally any prior art the applicants have been able to locate on this subject matter suggest purification of lactide by recrystallization or precipitation from a suitable solvent such as methanol. The difficulty with such a procedure is that there tends to be a commercially unacceptable loss of starting material and additionally it requires the handling and recovery of a large quantity of volatile solvents.

Accordingly there is a need for a better process for the purification of crude lactide.

The present invention seeks to overcome this need by providing a process for the melt recrystallization of lactide.

SUMMARY OF THE INVENTION

Accordingly the present invention provides a process for the melt recrystallization of lactide comprising:
  (i) heating a mixture of lactide isomers to a temperature of greater than 95° C. to form a melt;
  (ii) passing the melt through at least one recrystallizer cooled to a temperature from 45° to 90° C. to cause a lactide composition having a relative higher content of a targeted lactide isomer to crystallize on an interior surface of said at least one recrystallizer while maintaining a lactide composition having a relatively lower content of said targeted isomer and a higher content of impurities in the liquid phase; and
  (iii) separating said solid and liquid phases.

DETAILED DESCRIPTION

Generally, in the production of high molecular weight polylactic acid the targeted isomer will be the l-isomer. However, the targeted isomer could also be the m-isomer in which case the liquid phase would be segregated and become the feed stream for a separate crystallization stage. The crystal product of such separate crystallization stage would then be polymerization grade m-lactide.

Typically, fairly crude lactide, for example obtained from depolymerization of low molecular weight polylactic acid, comprises from 0.1 to 10.0% of carboxylic acid (e.g. not in the form of the cyclic dimer) and from 0.05 to 1.0 weight % of water. To obtain polylactic acid having a molecular weight in the range from 20,000 to 300,000, preferably from 50,000 to 200,000 by ring opening polymerization of lactide, it is necessary to start with a lactide having a considerably lower content of such impurities.

Figure 1:
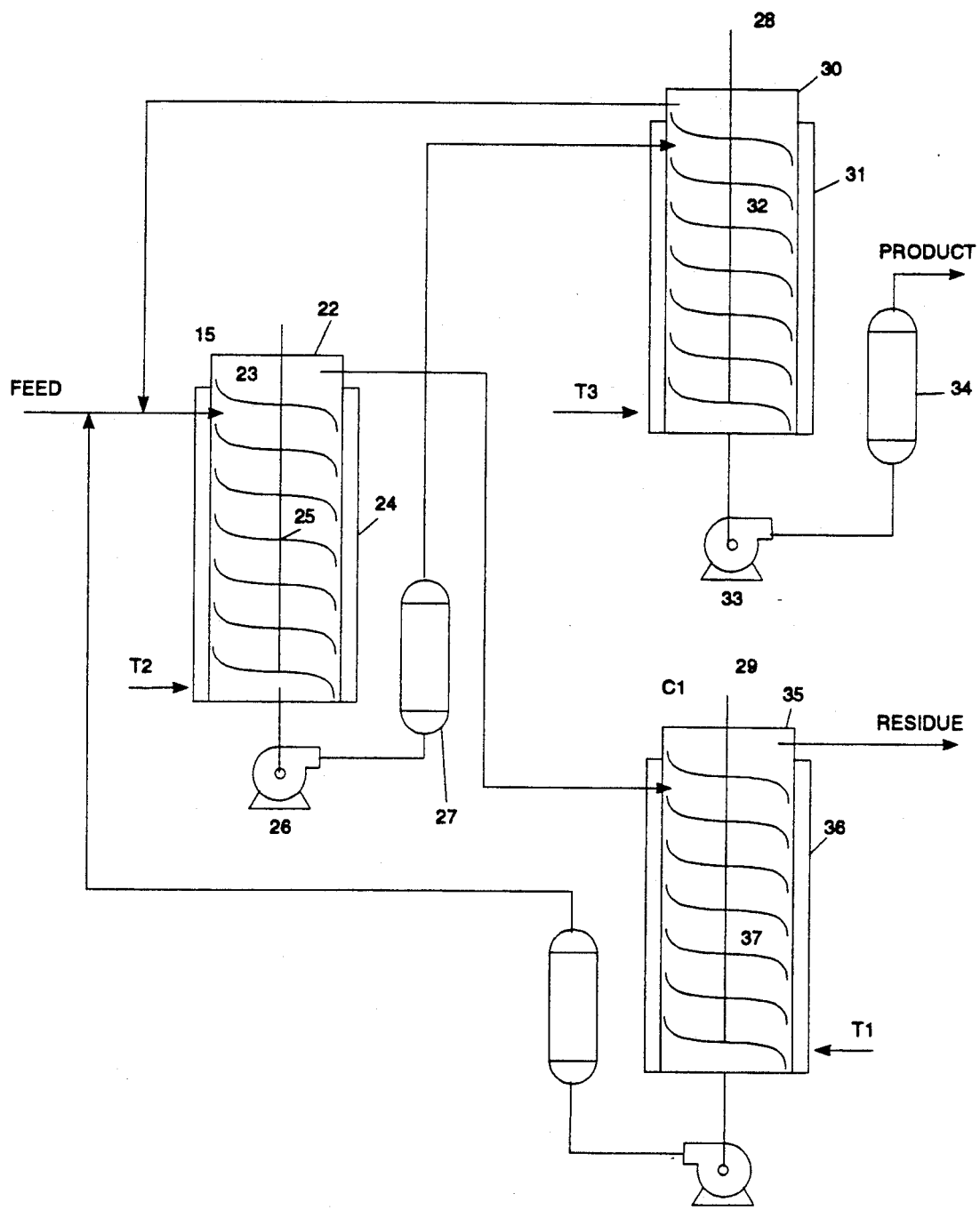
FIG. 1 is a schematic diagram of a three stage melt recrystallizer.
Figure 2:
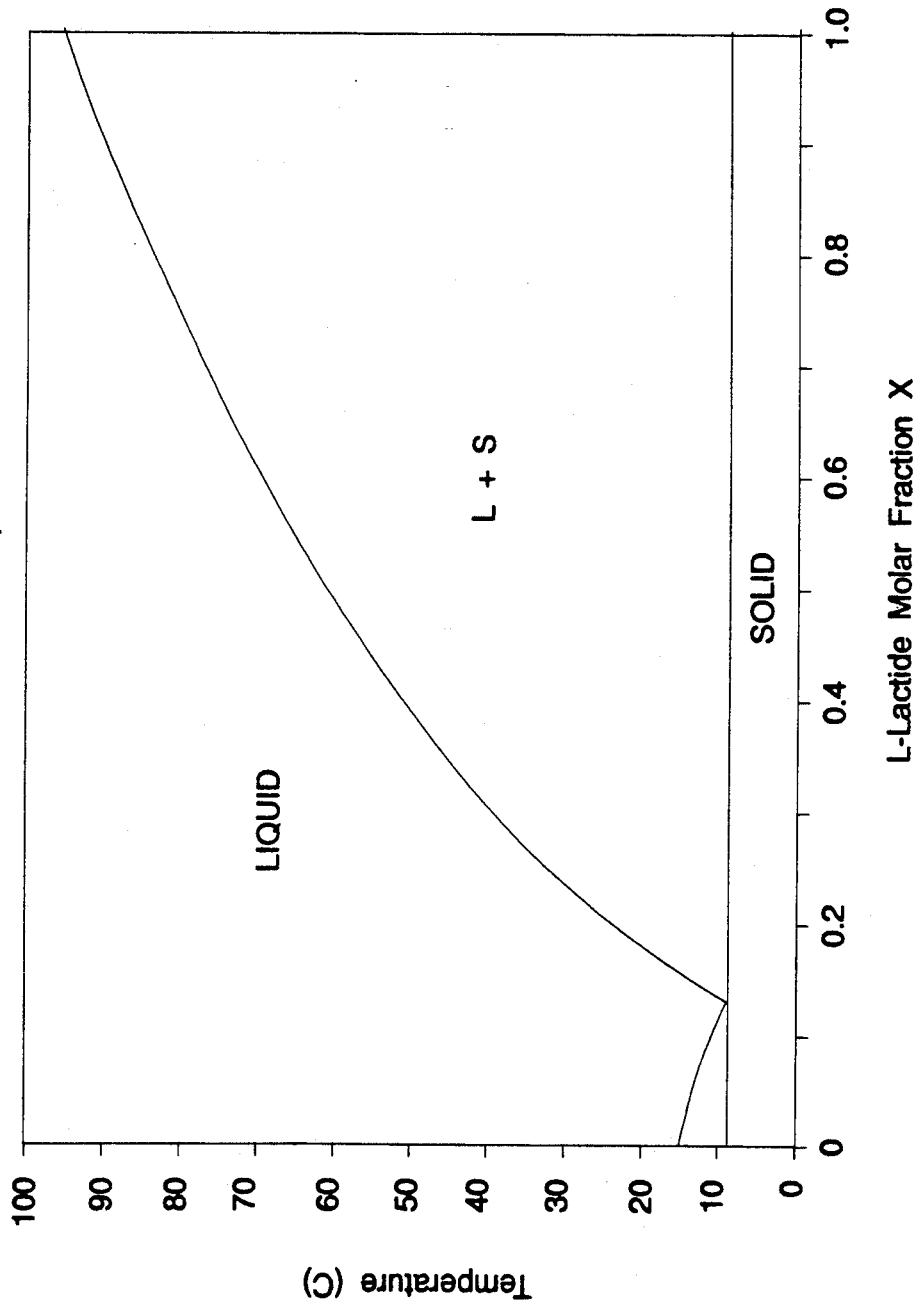
FIG. 2 is a phase diagram of the l-lactide/lactic acid solid liquid equilibrium.
Figure 3:
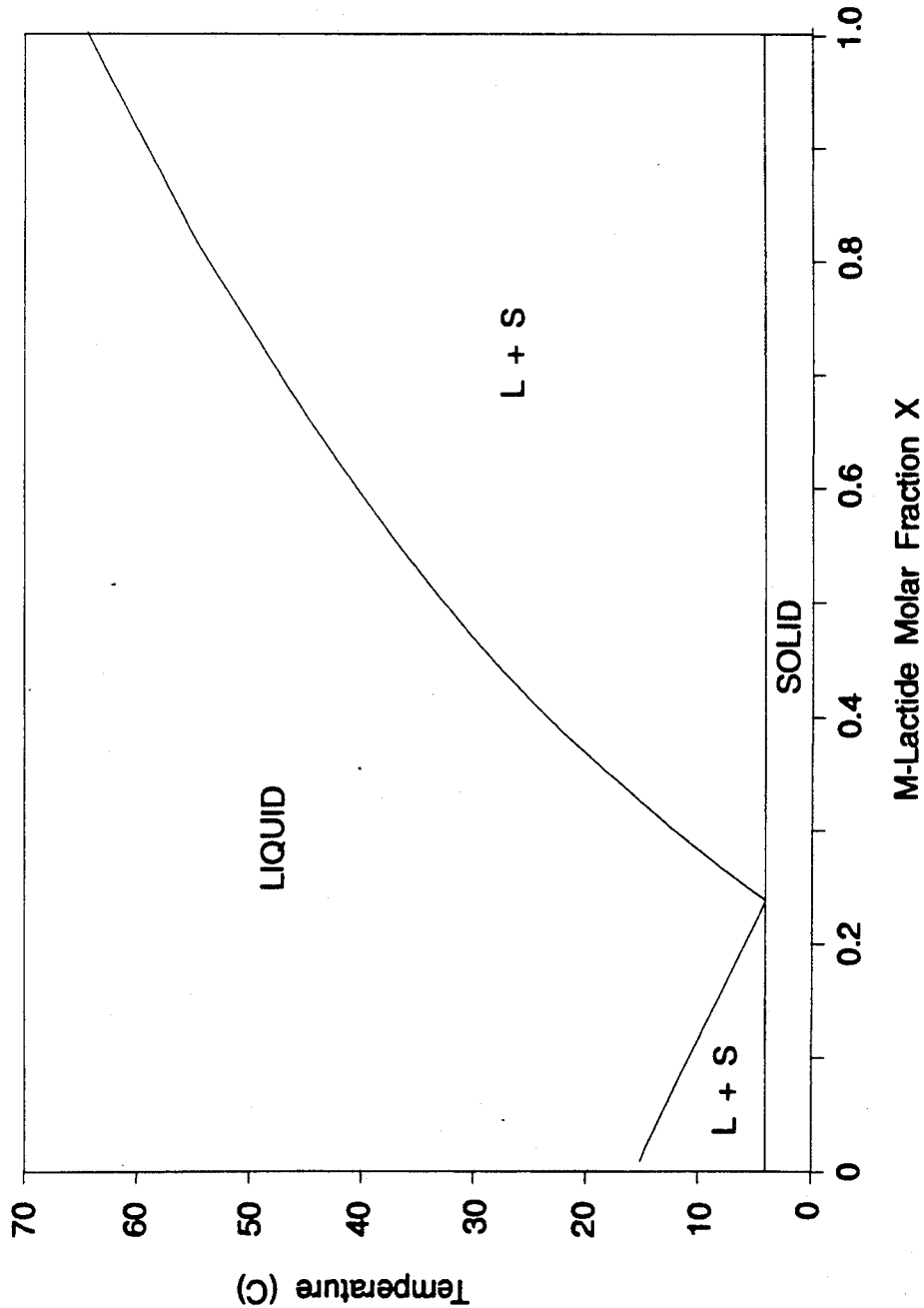
FIG. 3 is a phase diagram of the m-lactide/lactic acid solid liquid equilibrium.
Figure 4:
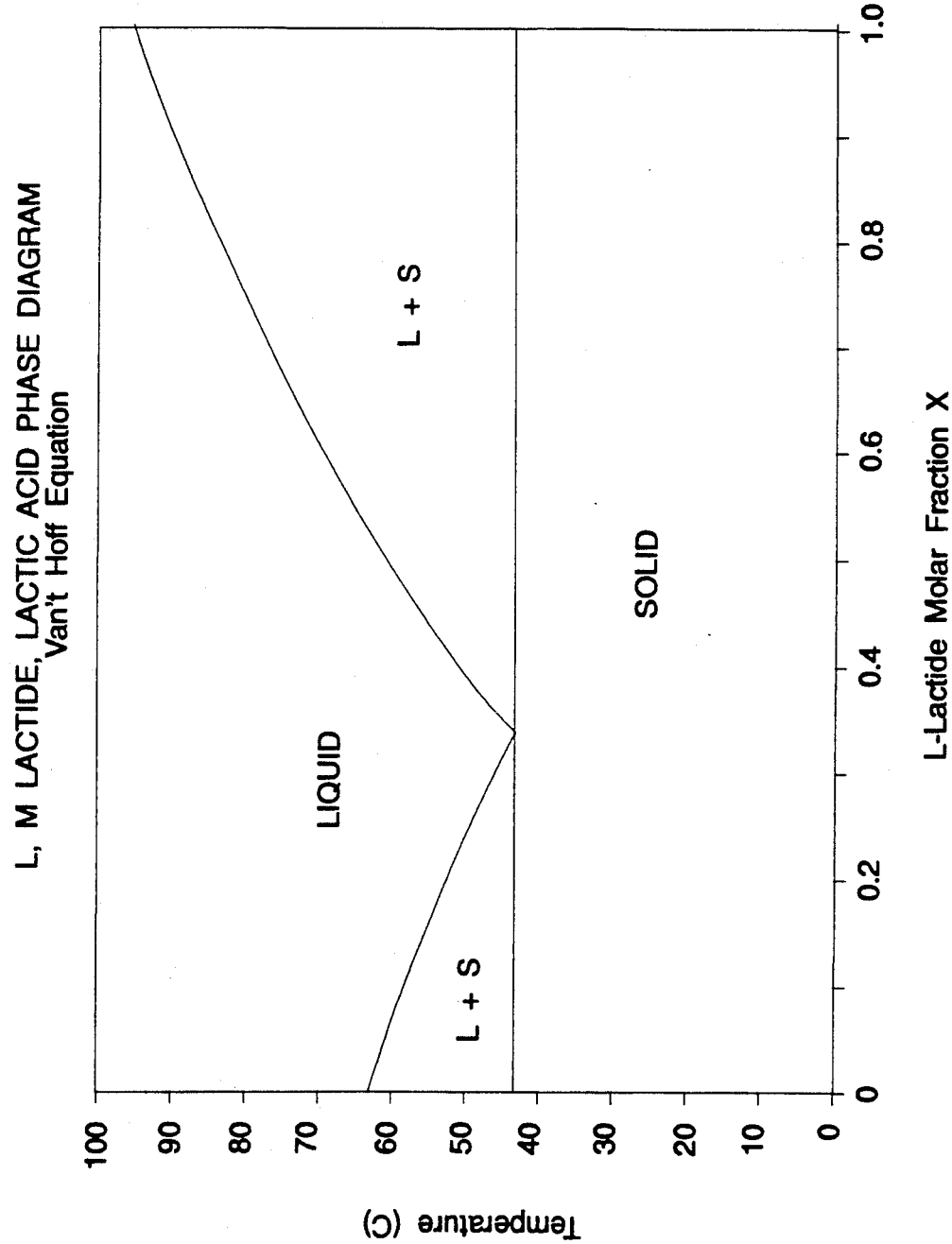
FIG. 4 is a phase diagram of the m- and l-lactide solid liquid equilibrium.
Figure 5:
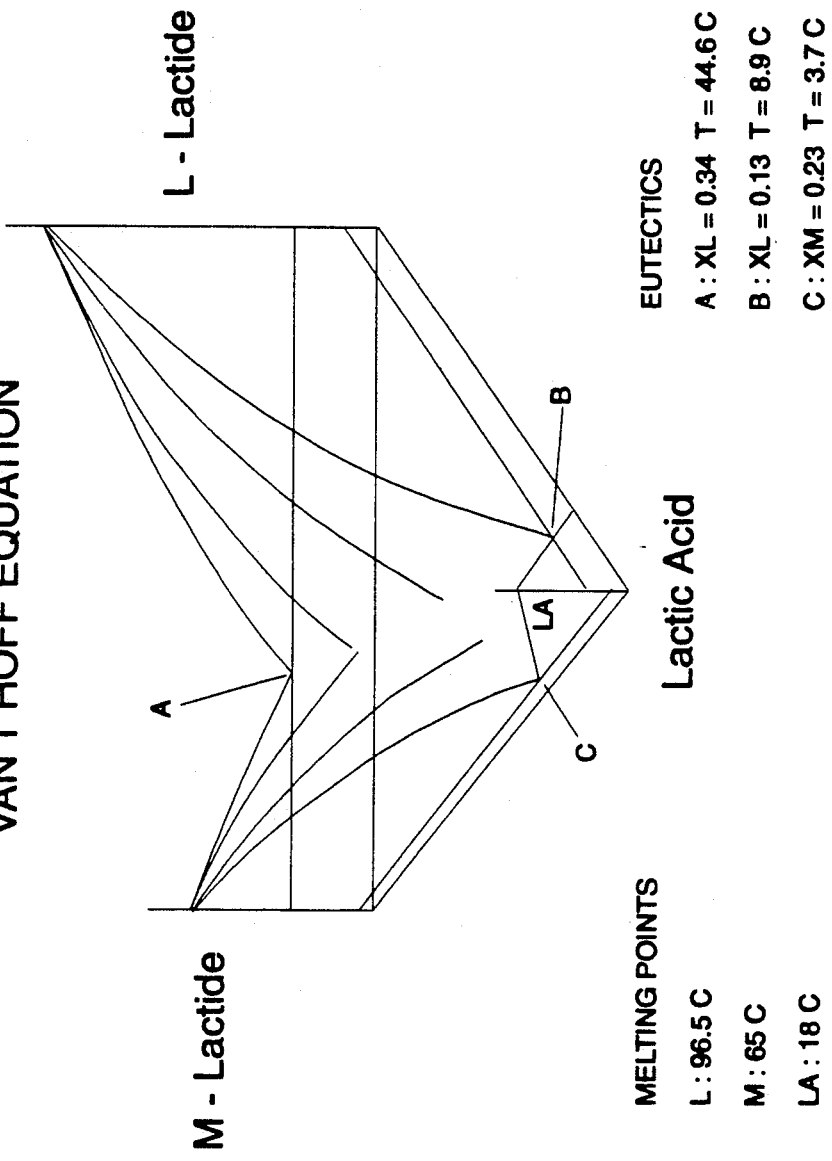
FIG. 5 is a phase diagram derived from Van'T Hoff's Equation for the three component system comprising l-lactide, m-lactide and lactic acid which shows contours for the solid liquid equilibrium and the eutectic points for the three two phase mixtures (e.g. m-lactide and lactic acid; l-lactide and lactic acid; and m-lactide and l-lactide as C, B, and A respectively) and the mole fraction of the lactide of the specified configuration (e.g. $X_L$ is mole fraction of l-lactide and $X_M$ is mole fraction of m-lactide).

The principle of melt recrystallization is best described by referring to FIGS. 2 through 4 which are two component liquid solid phase diagrams derived from Van T'hoff's equation and FIG. 5 which is a three dimensional representation of the contour surfaces for the liquid solid equilibrium for three component systems or mixtures indicating concentration of the components and temperature. FIGS. 2 through 4 show the liquid/liquid-solid (L+S)/and solid equilibriums for lactic acid, l-lactide, m-lactide and l,m-lactide (mixtures). While in some instances it may be desirable to use 100% pure m- or l-lactide typically the lactide polymerized will be a mixture of lactide having different configurations. The present invention seek to provide a purified lactide stream having a useful l-, m-ratio. In some cases there is a need to reduce the m-isomer. The m-isomer may, however, be present in the lactide in an amount from about 0.0 to 30.0, preferably from 0.5 to 25 weight %. Once the weight % or mole fraction of m-isomer permissible in the lactide mix is known or selected FIG. 4 will be used to determine the upper temperature limit of the recrystallization step. FIGS. 2 and 3 taken together show that with each recrystallization at a higher temperature more of the M-isomer will be removed from the solid phase (assuming that the composition is to the right of the eutectic point). From FIGS. 2, 3, and 4 suitable temperatures for the process can be selected.

Location of a system on the phase diagrams relative to the eutectic point is a function of the composition of the crude lactide stream. To be on the left side of the eutectic point, one would have to start with a composition which contained greater than about 65 weight % of m-lactide. The typical composition of crude lactide should have a ratio of l to m isomers from about 80:20, more preferably 90:10. Through each purification step the solid lactide or liquid solid slurry of lactide becomes richer in l-isomer and the liquid phase becomes leaner. Accordingly, in each step going up in purity (of l-isomer) the composition is moving more to the right of the eutectic point.

A continuous crystallizer consists generally of a vessel which is fitted with a cold surface. Typically the crystallizer will comprise one or more vessel in a series. Generally the temperatures in the recrystallizers may be from 45 to 90, preferably from 65° to 80° C. The product to be treated, in this case crude lactide having a l-, m-ratio from about 80:20 to 90:10 is heated to form a melt above the melting point of a lactide mixture having a targeted l,m ratio. The cool surface is held at the temperature to yield the desired composition of product. The compositions which are solid at that temperature from crystals or in some cases a slushy mass on the cool surface. Compositions which contain, in this case sufficient m-isomer remain liquid. The solid or slush, is removed from the cool surface, typically by a scraper or other suitable mechanical means. The specific gravity of the solid phase is higher than that of the (uncrystallized) liquid phase, thus after being removed from the cold surface this solid material sinks to the bottom of the crystallizer. The solid material is then pumped to zones of higher temperature increasing the purity (or richness of the l-isomer) of the solid phase. The liquid phase travels counter current to and often over the solid phase to extract any impurities, to zones of lower temperature, and in this case lower purity. Multiple crystallizers of this type can be arranged in series to provide the required purification of the crude lactide. One possible arrangement is shown schematically in the drawings.

The crude lactide is heated to a temperature to form a melt but not to degrade the lactide. Suitable temperatures will be greater than 95° and less than about 150° C., generally from 95° to 110°, preferably from 95° to 100° C. The crude lactide melt is fed to first recrystallizer 22. First recrystallizer 22 comprises a hollow cylinder 23 and a cooling jacket 24. A coolant at T2, in this case say 80° C. is circulated through cooling jacket 24. A lactide mixture containing about 0.80 to 0.90 mole fraction of l-isomer condenses or crystallizes on the inside of the cylinder 23 (see FIG. 5). The liquid fraction within cylinder 23 contains the remaining m-lactide, l-lactide, and other impurities because it won't crystallize out at that temperature, (see FIG. 4). The crystals are scraped off the interior of cylinder 23 by rotary scrapers 25 and precipitate through a solution of crude lactide melt. The crystals from the bottom of recrystallizer 22 are pumped by pump 26 through a heat exchanger 27 where they are heated to about 90° C.

The melt then enters a second recrystallizer 28 operated at 90° C. The effluent from the top of recrystallizer 22 passes to a cooler recrystallizer 29.

Recrystallizer 28 comprises a hollow cylinder 30 and a heat jacket 31. A coolant (heatant) circulates through heating jacket 31 to maintain the temperature within the cylinder at 90° C. Crystals of m-l lactide will form on the walls of cylinder 30. The crystals will have an l-isomer content of upwards of 0.90 mole % (see FIG. 3). The crystals are scraped off the walls by rotary scrapers 32 and precipitate through a solution of relatively less crude lactide. As the crystals precipitate they sweat and lose impurities. The proper mole percent of l-isomer is maintained in the crystals. It should be noted that small occlusions of m-isomer may be lost as the crystal falls through the solution. The crystals which precipitate to the bottom of recrystallizer 28 are pumped by pump 33 to a recovery zone. Often it is desirable to incorporate the recrystallization process of the present invention into a polymerization process. In such a case the purified lactide is pumped through heat exchanger 34 to one or more reactors.

In the alternative the crystals could be collected as solid lactide which could later be melted and used in reactors.

The effluent from the top of recrystallizer 22 may be recycled back to a cooler recrystallizer 29. Recrystallizer 29 comprises a hollow cylinder 35, and a cooling jacket 36. The coolant in this recrystallizer is maintained at a temperature of about 70° C. The crystals formed on the interior of cylinder 35 will have a higher content of m-isomer (about 0.6 mole %). The crystals are scraped off the interior wall of the cylinder by rotary scraper 37. The crystals may be returned to the feed to recrystallizer 22 or may be collected as solid lactide.

In a further optional embodiment prior to returning the bottom product of crystallizer 29 to recrystallizer 22, it may centrifuged to separate it into a solid fraction of higher purity and higher l-isomer content. This solid fraction may be blended with the crude lactide and fed to recrystallizer 22. This procedure may be applied to any bottom recycle stream. Similarly the effluent from recrystallizer 29 (rich in lactic acid) may be used as a feed for the preparation of crude lactide by the condensation of lactic acid to lactide.

Figure 6:
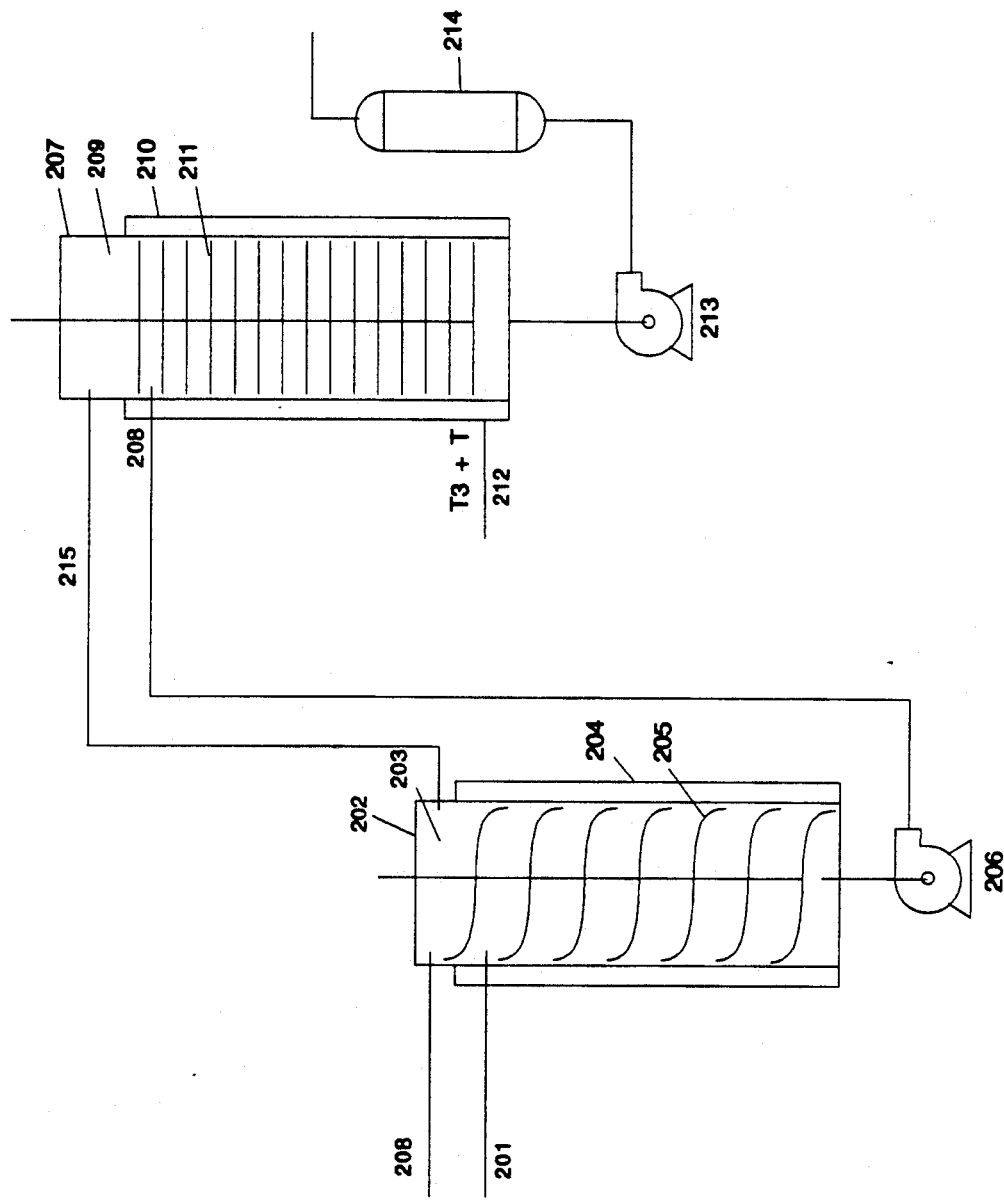
FIG. 6 is a schematic diagram of a recrystallizer and a rectifier.

In an alternate embodiment of the invention a single stage dedicated rectification column, of larger size could be added to treat the effluent from the last recrystallizer prior to polymerization. This embodiment is schematically illustrated in FIG. 6. The crystallizer operates as described above. In the rectifier the crystals from the crystallizer sink slowly, under mild crystallization to provide intimate contact between the liquid and solid phases and an additional degree of sweating and purification of the solid or crystal phase.

The process will be briefly described with reference to FIG. 6. In FIG. 6 a melt of a mixture of lactide forms feed stream 201 which enters crystallizer or recrystallizer 202. The feed stream 201 may come from an upstream recrystallizer and be relatively pure or it may be a melt of crude lactide. Recrystallizer 202 comprises a hollow cylinder 203 and a cooling jacket 204. A coolant at temperature T3 is circulated through the cooling jacket 204 to cool the interior of the cylinder to a temperature below the temperature of the melt. The mixture of m, and l-lactide which solidify at the temperature of the internal surface of the cylinder 203 forms crystals on the cooler interior surface of the cylinder 203. The crystals are scraped off the interior surface of the cylinder 203 by a rotary scraper 205. The crystals fall to the bottom of the recrystallizer and are pumped by pump 206 to the top of rectifier 207. The melt of lactide in the recrystallizer which contains a higher m-lactide content and other impurities leaves recrystallizer 203 as over head stream 208. This over head may be returned to an up stream recrystallizer or used for some other purpose such as the polymerization of lactide or it may be disposed of.

The product from recrystallizer 203 enters rectifier 207 at the top of the rectifier through a port 208. The rectifier 207 comprises a hollow cylinder 209, a heating jacket 210, and an agitator 211. In operation the rectifier is filled with a melt of slightly more impure lactide. A heatant or heating liquid 212 is circulated through the heating jacket at a temperature T3 plus a small increment T, preferably 1 to 5, more preferably 1° to 3° C. above the temperature of the fluid circulated through cooling jacket 204 of recrystallizer 202. From a practical point of view the heatant for the rectifier 207 may also act as the coolant for recrystallizer 202. The crystals from recrystallizer 202 slowly fall through the impure liquid melt in the rectifier. The agitator turns only slowly to avoid total or significant dissolution of the crystals yet provide good heat transfer between the liquid in the rectifier and the warmer surface of the interior walls of the rectifier. As the crystals fall through the liquid medium the outer surface of the crystals melts to release any occluded impurities or m-lactide. This sweating process increases the purity of the crystals. The crystals are pumped from the bottom of the rectifier by pump 213. Preferably the crystals are passed through a heat exchanger 214. Depending on the use of the crystals the heat exchanger may heat them to form a melt suitable for polymerization for example or cool them to ensure a solid product.

In the process illustrated in FIG. 6, the effluent from the overhead of rectifier 207 is returned to recrystallizer 202 by line 215.

While the recrystallization of lactide in a multi-stage recrystallizer has been described in a three step process the number of steps in the process may range from one to a suitable number depending on the degree of purity or composition of the lactide required. In a single stage recrystallizer the melt would be cooled and the liquid phase drawn off and the solid crystals recovered.

While the present invention has been described in terms of a continuous stepwise process it may also be carried out in one or more discontinuous batch process(es).

The present invention will now be illustrated by the following examples. Much of the experimental work was done using laboratory equipment. In the examples unless other wise indicated parts means parts by weight and % means weight %.

EXAMPLE 1

Purification of Crude Lactide—Static Experiment

A sample of crude lactide was melt crystallized in a single stage static method (e.g. a simple tube). A melt of crude lactide at a temperature of about 80° C., was maintained in a tube and purer lactide crystallized out on the side of the tube. The liquid residue and the relatively purer crude lactide crystals were analyzed. The results are setforth in Table 2.

TABLE 2

| | Melt Crystallization of Crude Lactide | | |
|---|---|---|---|
| Component | Untreated Crude 331-65 | Liquid Phase 332-12-C | Solid Phase 332-12-D |
| M (%) | 4.5 | 9.0 | 5.8 |
| L, D (%) | 91.5 | 89.9 | 93.4 |
| Lactic Acid (%) | 0.47 | 1.26 | 0.85 |
| Oligomers (%) | 3.0 | 1.3 | 0.8 |
| Water (ppm) | 2950 | 920 | 930 |

The results are ambivalent. There appears to have been some hydrolysis and racemisation during the process. However, the amount of oligomers and water in the "purer" crude lactide were significantly reduced. Given the unsophisticated procedure the results were sufficiently promising to warrant a further attempt using a dynamic apparatus.

EXAMPLE 2

Purification of Crude Lactide—Dynamic Experiment

A melt of crude lactide was maintained in a rotary evaporator at a temperature of 84° C. In the rotary evaporator the lactide crystals condensed out on the sides of the evaporator. The crystals were in a melt of less pure lactide. The liquid phase was removed. The impurities were "sweated" out of the more crystalline product at 87° C. At the end of the run the impure melt was separated from the more pure crystalline product. The untreated crude lactide, the liquid phase and the solid phase were analyzed. The results of the analysis are setforth in Table 3.

TABLE 3

| Component | Untreated Crude % | Liquid Phase % | Solid Phase % |
|---|---|---|---|
| M (%) | 16.55 | 30.96 | 3.45 |
| L, D (%) | 83.45 | 69.31 | 96.55 |
| Lactic Acid (%) | 8.43 | 12.27 | 0.88 |

These results show that using a fairly simple dynamic device it is possible to obtain about an order of magnitude reduction in impurities, and particularly in lactic acid per pass through a melt recrystallizer. Accordingly, it is apparent to one skilled in the art that a multi stage-melt recrystallizer would be a suitable device to significantly improve the purity of crude lactide in a continuous manner.

What is claimed is:

1. A process for the melt recrystallization of lactide comprising:
(i) heating lactide to a temperature of greater than 95° C. to form a melt;

(ii) passing the melt through at least one recrystallizer cooled to a temperature from 45° to 90° C. to cause a lactide composition having a relative higher content of a targeted isomer to crystallize on an interior surface of said at least one recrystallizer while maintaining a lactide composition having a relatively lower content of said targeted isomer and a relatively higher content of impurities in the liquid phase; and (iii) separating said solid and liquid phases.

2. The process according to claim 1, wherein said melt recrystallization is conducted using a series of at least two recrystallizers.

3. The process according to claim 2, wherein said recrystallizers are counter current recrystallizers.

4. The process according to claim 3, wherein the crude lactide is fed to one or more recrystallizers in a series and cooled to a temperature from 45° to 90° C. the crystallized product from any recrystallizer is said series except the last, being fed to an immediately subsequent recrystallizer, operated at a temperature at least 3° C. higher than said immediately prior crystallizer, the uncrystallized melt effluent from any recrystallizer in said series, except the first recrystallizer being returned to the immediately prior recrystallizer, the uncrystallized melt from said first recrystallizer being collected, and the product from the last recrystallizer being collected.

5. The process according to claim 4, wherein said series of recrystallizers are cooled to a temperature from 65° to 80° C.

6. The process according to claim 5, wherein the uncrystallized melt from any recrystallizer in the series except the first is treated in a centrifuge to separate a fraction of higher purity which is returned to the immediately prior crystallizer.

7. The process according to claim 5, wherein said targeted isomer is the l-isomer.

8. The process according to claim 5, wherein said targeted isomer is the m-isomer.

9. The process according to claim 1, wherein the recrystallization is carried out in a continuous manner.

10. The process according to claim 1, wherein the recrystallization is carried out in a batch manner.

11. The process according to claim 7, wherein the recrystallization is carried out in two or more continuous recrystallizers.

12. The process according to claim 7, wherein the recrystallization is carried out in one or more batch recrystallization steps.

13. The process according to claim 8, wherein the recrystallization is carried out in two or more continuous recrystallizers.

14. The process according to claim 8, wherein the recrystallization is carried out in one or more batch recrystallization steps.

15. The process according to claim 1 further comprising passing said solid phase through a rectifier at a temperature from 1° to 5° C. above the crystallization temperature of said solid phase.

16. The process according to claim 2 further comprising passing said solid phase through a rectifier at a temperature from 1° to 5° C. above the crystallization temperature of said solid phase.

17. The process according to claim 10 further comprising passing said solid phase through a rectifier at a temperature from 1° to 5° C. above the crystallization temperature of said solid phase.

* * * * *